US006258930B1

(12) United States Patent
Gauch et al.

(10) Patent No.: US 6,258,930 B1
(45) Date of Patent: Jul. 10, 2001

(54) PROCESS AND APPARATUS FOR BREAKING DOWN BIOLOGICAL MATERIAL

(75) Inventors: Simone Gauch, Pasadena, CA (US); Helge Bastian, Mettmann (DE); Manfred Roord; Uwe Orth, both of Haan (DE); Radu Anghel, Düsseldorf (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/517,437

(22) Filed: Mar. 2, 2000

(30) Foreign Application Priority Data

Mar. 4, 1999 (EP) .................................................. 99104360

(51) Int. Cl.⁷ .......................... C12P 21/02; C07H 21/02; C07H 21/04; B02C 17/14
(52) U.S. Cl. ......................... 530/300; 530/350; 536/23.1; 241/180
(58) Field of Search ............................. 241/180; 530/300, 530/350; 536/22.1, 23.1

(56) References Cited

U.S. PATENT DOCUMENTS

| 4,466,554 | 8/1984 | Hanacek et al. . |
| 4,877,830 | 10/1989 | Döbeli et al. . |
| 5,047,513 | 9/1991 | Döbeli et al. . |
| 5,513,809 | 5/1996 | Perker . |
| 5,520,850 | 5/1996 | Chaloner-Gill et al. . |
| 5,567,326 | 10/1996 | Ekenberg et al. . |
| 5,707,861 | 1/1998 | Sherman et al. . |

FOREIGN PATENT DOCUMENTS

| 197 55 960 | 11/1998 | (DE) . |
| 0 306 276 A2 | 3/1989 | (EP) . |
| WO 98/20164A | 5/1998 | (WO) . |

OTHER PUBLICATIONS

Bresters, D. et al., 1994, *J. Med. Virol.* 43 (3), 262–268.
Collins M.L. et al., 1997, *Nucl. Acids Res.* 25 (15), 2979–3984.
Holland, P.M. et al., 1991, *Proc. Natl. Acad. Sci. USA* 88, 7276–7280.
Kievits, T. et al., 1991, *J. Virol. Meth.* 35, 273–286.
Livak, K.J. et al., 1995, *PCR Methods Applic.* 4, 357–362.
Mixer Mill MM 2000 technical brochure (F. Kurt Retsch GmbH & Co. KG, Rheinische Strasse 36, D–42781, Haan, Germany, Aug. 1995).
Taberlet et al., 1991, *Plant Mol. Biol.*, 17(5): 1105–1109.
Uyttendaele, M. et al., 1994, *J. Appl. Bacteriol.* 77, 694–701.

*Primary Examiner*—James Ketter
(74) *Attorney, Agent, or Firm*—Leon R. Yankwich; Thomas R. Berka

(57) ABSTRACT

The use of multi-well blocks with more than 10 wells is suggested for breaking down biological samples in a ball mill, wherein the process which is to be carried out provides that the biological sample, disposed in a multi-well block with more than 10 wells, is broken down in a ball mill and that following this, proteins and/or nucleic acids are isolated. With the ball mill necessary for this task, with milling containers fixed thereto in a holder (10), the milling containers are designed as uniform well blocks (16) and can be fixed in a form-locking manner into the adapted, twist-preventing holder (10).

18 Claims, 3 Drawing Sheets

PROCESS AND APPARATUS FOR BREAKING DOWN BIOLOGICAL MATERIAL

SPECIFICATION

The analysis of biological materials, particularly using nucleic acid-based methods, is becoming increasingly important in many fields, particularly in basic biological and medical research, and especially in applications such as molecular diagnostics or animal husbandry and horticulture.

In order to be able to analyse biological materials first of all the biological sample material has to be broken down. First of all, the cell structure has to be destroyed in order to allow biological molecules to be isolated. Starting materials such as plants, bacteria or yeasts, moreover, have a highly resistant cell wall which makes it even more difficult to release the molecules which are to be analysed, particularly nucleic acids and/or proteins.

A decomposition process which is suitable for breaking down these materials should ensure that the samples can be broken down very rapidly, if possible within a few seconds, and at the same time in a highly efficient manner. This is particularly important when isolating nucleic acids, particularly RNA, since many gene expression analysis methods require quantitative isolation of intact nucleic acid, particularly RNA. RNA is a material which degrades very rapidly after the destruction of the cell structure and is therefore impossible to analyse when unsuitable slow methods of breaking down are used.

Numerous applications of nucleic acid-based analysis such as tissue typing, screening of new active substances for pharmaceuticals or quality control of seeds are characterised by a high throughput of samples and the use of small amounts of starting material. For many high throughput applications, the breaking down of the biological sample is the limiting step, since there are already automated systems available for further processing the sample once it has been broken down, e.g. the BioRobot made by QIAGEN.

A number of mechanical breaking down processes are described in the prior art. One such apparatus is described in the company brochure of the applicants Retsch "Vibration Mill ("Schwingmühle") MM 2000"; insofar as it discusses the breaking up of biological cells, holding means designed to hold five or ten single-use test tubes can be clamped in the holder of the vibrating ball mill, the test tubes being inserted into the holding means for the break down process and at least one glass bead being placed into each individual test tube in order to break down the biological material. The mount provided on the vibrating ball mill for clamping the holding device in place or, if the vibrating ball mill is used for other grinding purposes, for clamping suitable grinding cups, consists of a U-shaped frame with a baseplate attached to the drive of the vibrating ball mill and with two opposing, planar retaining arms which hold the holding device or grinding cup between them, one of which is movably mounted and can be brought into clamping abutment on the holding device or grinding cup by means of an adjustment and clamping screw.

This known apparatus has the disadvantage that the break down of biological materials is not reproducible in different batches and therefore cannot be evaluated with sufficient accuracy, as the holding device in question cannot be clamped in exactly the same position between the holding arms of the mount and may change its position, however slightly, even during a breaking down process, depending on the tension applied by means of the adjustment and clamping screw; however, the position of the spindle of the holding device is not thereby fixed in spatial relationship with the drive of the vibrating ball mill. However, since the amplitude of the oscillating movement acting on the holding device during the break down adjusts itself as a function of the spatial relationship of the axis of the holding device to the drive, different amounts of energy are put into the grinding means with different degrees of tension or with a varying tension, which means that the biological material is broken down to different extents. A further disadvantage is that the break down capacity, for a batch of five or ten test tubes, is too little, by design.

A high sample throughput is particularly important for use in nucleic acid-based analysis methods and diagnostic processes. In addition, the break down process should avoid cross-contamination.

Hitherto, the prior art has not described any break down processes which would enable more than ten samples to be subjected to simultaneous, rapid, efficient breaking up as free from cross-contamination as possible.

The aim of the present invention is therefore to provide a rapid and effective mechanical method of breaking down, including an apparatus suitable for this purpose, which allows more than ten samples to be subjected to simultaneous, rapid and efficient breaking down as free from cross-contamination as possible.

This problem is solved according to the invention by the use of multi-well blocks containing more than ten wells for breaking down biological samples in a vibrating ball mill, and by the process recited in claim 2, as described in more detail hereinafter, and by the apparatus described in claim 9. Preferred embodiments of the process according to the invention and the apparatus according to the invention are recited in the subclaims.

Specifically, the invention relates to use of multi-well blocks having more than 10 wells for breaking down biological samples in a vibrating ball mill.

The terms "biological material" or "biological sample" for the purposes of the present invention denote all materials which are produced by biological organisms or can be isolated from them; in particular, they denote materials which contain nucleic acids and/or proteins. The term "biological material" or "biological sample" includes untreated or pretreated samples, e.g. plasma, body fluids, particularly blood, sputum, urine, faeces, sperm, cells or cell cultures, serum, leukocyte fractions, smears, tissue samples of all kinds, plants and parts of plants, microorganisms such as bacteria, viruses such as cytomegalo virus, HIV, hepatitis B, hepatitis C, hepatitis δ virus, yeasts, embryos, fungi, cell-free sample material, etc. The term "biological sample" also includes both a mixture of the abovementioned samples such as fungus-infected plants or whole human blood containing mycobacteria as well as food samples which contain free or bound nucleic acids or cells containing nucleic acids, environmental samples which contain free or bound nucleic acids or cells containing nucleic acids. Pretreated biological samples may be, for example, heat treated —frozen, dried, etc., or chemically treated, e.g. fixed in suitable chemicals such as formalin, alcohol, etc.

Biological molecules for the purposes of the present invention are organic molecules or derivatives thereof which are part of living cells or organisms, particularly nucleic acids and/or proteins, particularly DNA and/or RNA.

The term nucleic acids for the purposes of the present invention includes all possible kinds of nucleic acids such as deoxyribonucleic acid (DNA), ribonucleic acid of all lengths and configurations, such as double-stranded, single-stranded, circular and linear, branched, etc., plasmids, viral and bacterial DNA and RNA as well as genomic or other non-genomic DNA and RNA from animal and plant cells or other eukaryotes, t-RNA, mRNA in processed and unprocessed form, hn-RNA, rRNA and cDNA and all other conceivable nucleic acids. In addition, within the scope of the present invention, the definition includes a sample which contains nucleic acid or a sample or mixture of samples which contains nucleic acid, which may be used as suitable educts for "downstream applications" such as in vitro transcription, PCR reactions or cDNA syntheses.

The vibrating ball mill intended for using multi-well blocks is based on a vibrating ball mill having containers to be clamped thereon in a U-shaped holder having two opposing holding arms, one of the holding arms being movably mounted in order to clamp the grinding container and having an adjusting and clamping screw, whilst individual grinding members are placed in the containers in order to apply energy for the comminution process. The underlying concept of the invention is that the grinding containers are constructed as unified blocks of wells with a plurality of grinding chambers incorporated therein and closed off by means of a lid placed on the well block or by means of a plurality of lids and the well blocks can be fixed by interlocking engagement in the holder, which has means to prevent rotation, by means of aligned cams projecting above the plane thereof, and in that the holding arms of the holder each have a recess for interlockingly receiving the cams, which corresponds in depth to the height of the cams.

Well blocks having different numbers and configurations of receiving chambers (wells) provided therein are known as storage containers and reaction containers for samples of biological material, e.g. from the company brochure "Qiagen Product Guide 1997, p. 135 " issued by QIAGEN GmbH of Hilden. These well blocks which may contain 96 wells, for example, are made of thin-walled injection moulded plastics and can be closed off using a sheet of adhesive foil placed thereon as a cover.

One advantage of the invention is that the well blocks which have hitherto been used purely for storage purposes can themselves act as containers, particularly grinding containers for the breaking down of biological material, so that on the one hand the capacity of the apparatus is increased and on the other hand there is no need for the biological material which has been broken up to be transferred from test tubes into the individual wells of the storage containers for further processing or analysis, for example. The interlocking engagement of the well blocks in the holder, achieved by means of the cams engaging in the recesses in the retaining arms, ensures a clearly defined and hence reproducible positioning of the well blocks in the holder, so that the results of different breaking down processes are comparable on the grounds of an equal energy input. Since the depth of the recesses is matched to the height of the cams, the well blocks are securely located in the holder even when transverse acceleration is applied.

According to one embodiment of the invention, a cam is mounted on the base and lid of the well blocks, so as to project above the plane thereof; it goes without saying that the base and lid must be made stable enough so that the grinding means provided in the wells do not break through the base or lid.

Alternatively, the base of the well block in question may have a cam projecting above its plane and an adapter plate interlockingly engaging over the lid, with a cam projecting above the plane thereof; this has the advantage that different well blocks of different heights can be clamped in the holder by means of the adapter plate engaging over the lid, different thicknesses of adapter plates being used depending on the height of the well blocks. The adapter plate may itself also act as the lid.

In a preferred embodiment of the invention, the cams engaging in the recesses in the retaining arms of the holder are each formed on an adapter plate interlockingly engaging over the base or lid of the well block which is to be clamped in place to act as a grinding container. This has the advantage that well blocks which have hitherto been used as storage containers can be used directly, without modifications, for the breaking down operation, by inserting these well blocks between two adapter plates and clamping the adapter plates in the holder of the vibrating ball mill. The adapter plates provide the necessary support for the thin-walled base or a thin-walled or foil-like lid, so that the grinding means located in the wells do not penetrate the base and/or lid of the well blocks. As described above, adapter plates of different thickness may be used, depending on the height of the well blocks; in particular, one of the adapter plates may be constructed as the base adapter plate of constant configuration whilst the other associated adapter plate can be adjusted to the height of the particular well block which is to be inserted. To ensure full support for the base of the well block, which has an upstand all round it from the injection moulding process by which it was made, the adapter plate engaging over the base may have a groove to accommodate this upstand.

In order to form the rotation prevention means, the cams may be arranged as rotation prevention means so that the well block clamped in the holder rests on the baseplate of the U-shaped holder; alternatively, the cams and recess may be shaped so as to correspond to one another in profile. Where there is a problem of placing the grinding means in the individual wells, when using well blocks containing a fairly large number of wells, e.g. 96 wells, as mentioned earlier, or 384 wells per block, according to one embodiment of the invention a plate is provided, which is to be oriented on the well block, having openings associated with the individual grinding chambers of the well block and having a slide movably mounted on the plate and forming a movable base for the openings in the plate for holding the grinding means placed in the openings. The grinding means may then expediently be constructed, in known manner, as beads of a suitable material.

For breaking down biological samples, grinding means of suitable materials are used, particularly glass or ceramics, especially sintered ceramics, more particularly hard porcelain, zirconium oxide, aluminium oxide, as well as rock minerals, particularly marble, agate and also metals, particularly stainless steel, tungsten carbide and suitable plastics, particularly polyamide, Teflon and two-phase systems, especially Teflon-coated steel grinders.

The size and/or number of grinders used according to the invention is determined by the geometry of the grinding space and/or the biological sample used. For breaking down biological samples it is preferable to use one or more grinders in the form of beads or balls, more preferably one or more beads or balls consisting of the abovementioned materials.

In a preferred embodiment, animal and/or plant tissue is broken down using beads or balls, preferably one or more beads or balls having a specific gravity of $\geq 5$ g/cm$^3$, most preferably one or more balls of steel or tungsten carbide in a grinding chamber, most preferably a round-bottomed grinding chamber.

The apparatus according to the invention is pre-eminently suitable for the simultaneous parallel breaking down of very small volumes of sample, particularly in the multi-well format, especially using standard commercial 96-well or 384-well plates.

Another preferred embodiment of the present invention is the use of the apparatus according to the invention for breaking down biological samples for further isolating biological molecules, particularly proteins and/or nucleic acids, more especially DNA and/or RNA.

Biological samples are preferably broken down in the presence of adjuvants which have a lysing effect in suitable concentrations, hereinafter referred to as "lysing agents", particularly in the presence of detergents and/or chaotropic salts; it is particularly advantageous to put in additional substances which, in suitable concentrations, prevent the destruction and/or modification of the biological molecules which are to be isolated, and are hereinafter referred to as "stabilisers".

The destruction and/or modification of the biological molecules to be isolated is preferably prevented by stabilisers which prevent destruction by enzymes, especially nucleases and/or proteases, more particularly liquid nitrogen and/or complexing agents, especially chelating substances, particularly EDTA and/or detergents, especially SDS and/or salts, particularly chaotropic salts and/or antioxidants.

In another preferred embodiment of the present invention, the biological sample is broken down in the presence of a lysing agent and a stabiliser. The cells are simultaneously lysed and the biological molecules released are protected from breakdown/destruction. The biological molecules released, particularly proteins and/or nucleic acids, especially DNA and/or RNA, can subsequently be isolated.

In another embodiment, the apparatus described is preferably suitable for breaking down pretreated biological material, particularly biological material in a frozen state, the breaking up taking place in the frozen state, particularly under liquid nitrogen. This method of breaking up is advantageously suitable for isolating RNA, since the nucleases are inhibited in this process, in particular.

The abovementioned apparatus and its use, particularly in the preferred embodiments mentioned, is ideally suited to the preparation of samples for subsequent high throughput analysis, particularly on automated platforms, particularly platforms resembling the BioRobot made by QIAGEN.

The nucleic acids prepared using the process according to the invention are particularly suitable for manipulating biological molecules, particularly for amplifying nucleic acids, especially for PCR, NASBA, Strand Displacement Amplification, Ligase Chain Reaction (LCR), for use in diagnostics, especially for use in methods of diagnosis which are characterised in that the nucleic acid released by the process according to the invention is amplified in a succeeding step and then and/or at the same time the nucleic acid or acids amplified is or are detected (e.g. Holland, P. M. et al., 1991, Proc. Natl. Acad. Sci. 88, 7276–7280; Livak, K. J. et al., 1995, PCR Methods Applic. 4, 357–362; Kievits, T. et al., 1991, J. Virol. Meth. 35, 273–286; Uyttendaele, M. et al., 1994, J. Appl. Bacteriol. 77, 694–701).

Moreover, the nucleic acids made available by the process according to the invention are particularly suitable for signal amplification based on a reaction of hybridisation, characterised in particular in that the nucleic acids prepared by the process according to the invention are brought into contact with "branched nucleic acids", particularly branched DNA and/or branched RNA and/or corresponding dendrimers of nucleic acids, as described in the following references (e.g. Bresters, D. et al., 1994, J. Med. Virol. 43 (3), 252–286; Collins M. L. et al., 1997, Nucl. Acids Res. 25 (15), 2979–3984), and the signal produced is detected.

Another preferred embodiment of the present invention is a process which comprises the following steps: breaking down the samples using the apparatus according to the invention, concentrating and/or isolating the nucleic acids, particularly DNA and/or RNA, optionally manipulating the nucleic acid, particularly amplifying nucleic acids, most especially by PCR, NASBA, RT-PCR or other suitable methods, and optionally thereafter analysing the nucleic acids thus obtained.

Another preferred embodiment of the present invention is the following process:

breaking down the samples using the apparatus according to the invention, and subsequently isolating and/or analysing the proteins, particularly by affinity chromatography.

Preferred methods of affinity chromatography are methods based on antibodies and/or metal affinity systems, particularly the metals/histidine system, particularly the Ni-NTA/6His system, as described for example in U.S. Pat. Nos. 5,047,513; 4,877,830 and 5,520,850.

Using the process according to the invention it is thus possible to purify and/or analyse large amounts of sample material in a short time, particularly if the process described is also automated.

The drawings show an embodiment exemplifying the apparatus according to the invention which is described hereinafter. In the drawings.

Figure 1:
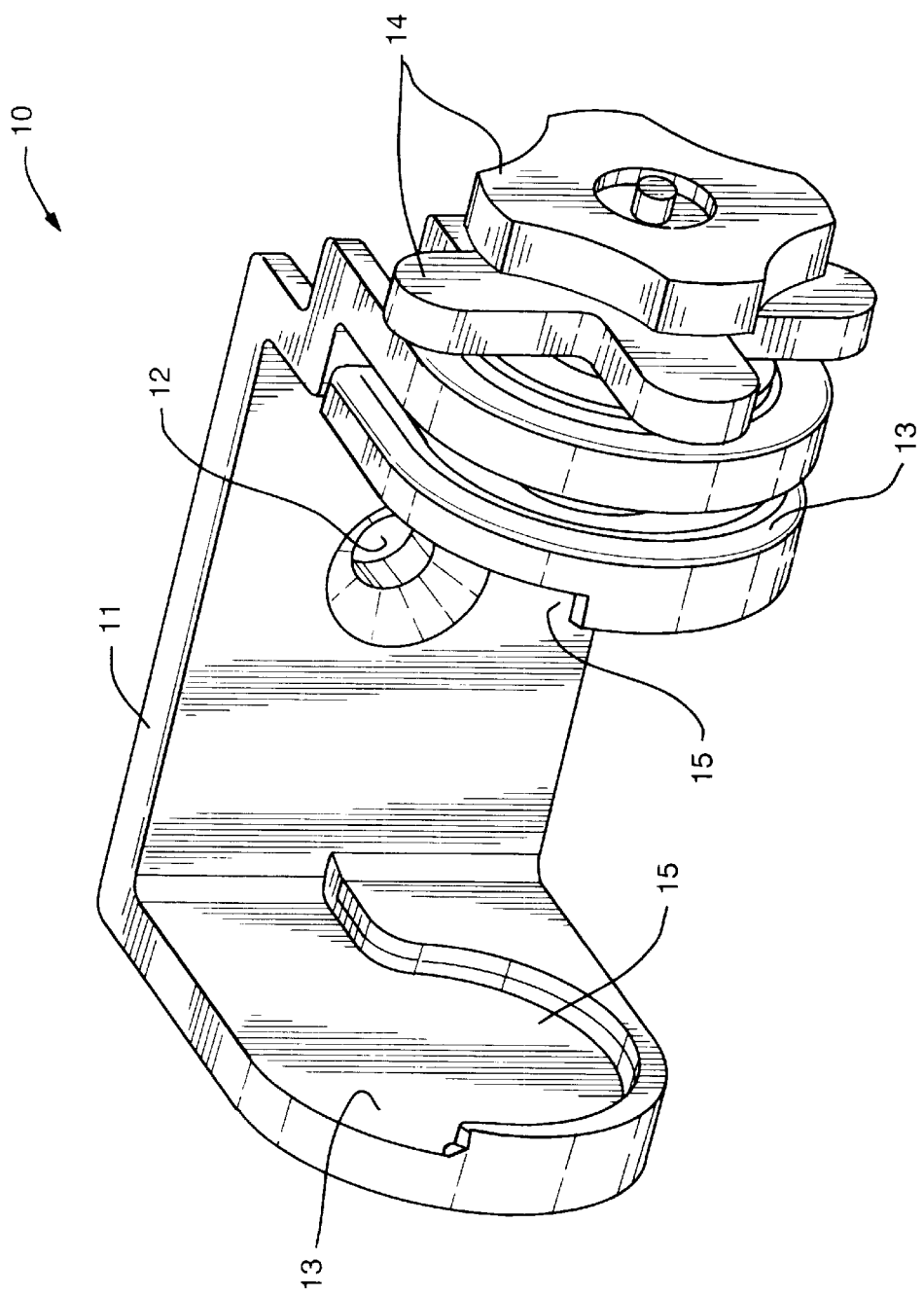
FIG. 1 shows the holder of a vibrating ball mill, shown in detail.

The holder 10 shown in detail in FIG. 1 is of U-shaped construction with a baseplate 11 having a fixing hole 12 for attaching the holder 10 to the drive of the vibrating ball mill (not show). Protruding from the baseplate 11 are two retaining arms 13, one retaining arm 13 being movably mounted and adjustable and fixable by means of an adjustment and clamping screw 14. The two retaining arms 13 each have a recess 15 for interlockingly receiving cams which are suitably provided on the grinding containers to be inserted, the recesses 15 being open over about half of their circumference so that the grinding containers with the cams provided thereon can be inserted in the recesses 15 from the open side.

Figure 2:
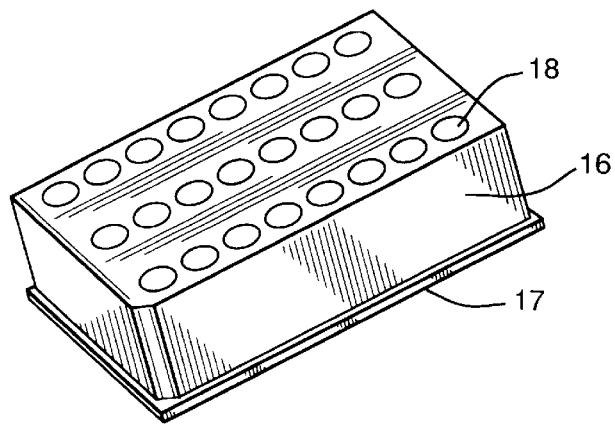
FIG. 2 shows a well block, in a detailed view, with the wells open.

In FIG. 2, the well blocks 16 provided as grinding containers are shown in detail, with individual grinding chambers constructed in the form of so-called wells 18. Preferably a well block 16 of this kind has a total of ninety-six wells 18.

Figure 3:
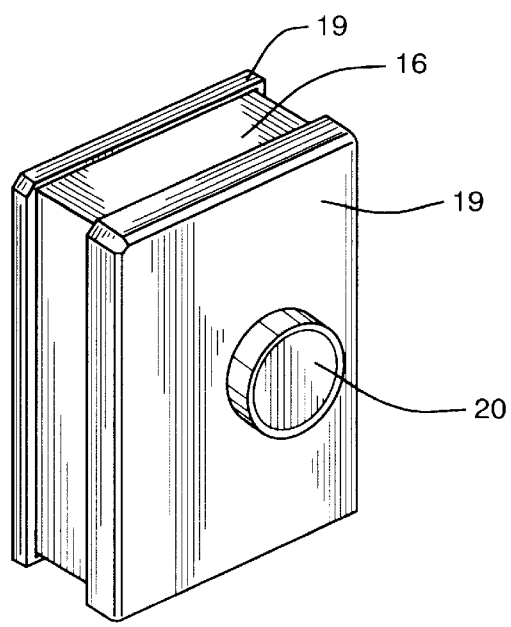
FIG. 3 shows a well block inserted between two adapter plates for use in the holder according to FIG. 1.

As can be seen from FIG. 3, the well block 16 shown in FIG. 2 is clamped in the holder 10 shown in FIG. 1 by means of two adapter plates 19 which engage interlockingly over the base 17 and top of the well block 16, optionally with a lid formed thereon, and thus secure the well block 16 between them. On the outside of each adapter plate 19 is a cam 20 protruding above the plane thereof, which is adapted in its shape and dimensions to the recesses 15 in the retaining arms 13 of the holder 10, so that the adapter plates 19 can be placed between the retaining arms 13, after which the movable retaining arm 13 is brought into a position of abutment on the associated adapter plate 19 by means of the adjustment and clamping screw 14.

Figure 4:
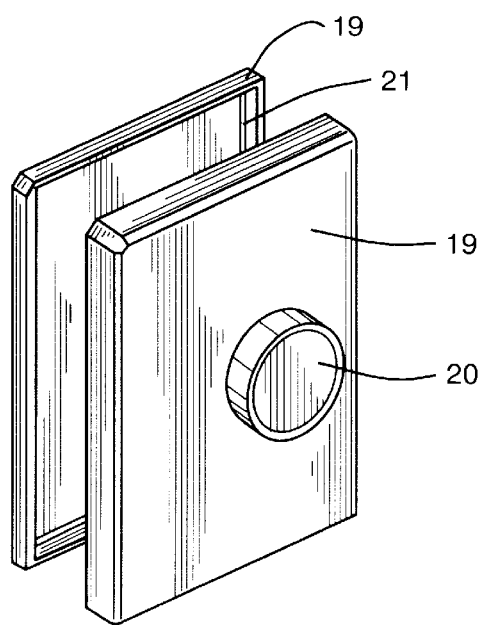
FIG. 4 shows the two adapter plates according to FIG. 3 without the well block placed between them.

As can be seen as an additional detail in FIG. 4, the adapter plate 19 which receives the base 17 of the well block 16 has a groove 21 running round it for accommodating an upstand projecting from the base 17 of the well block 16, which is normally there as a result of the manufacture of the well block 16 by the injection moulding method. This ensures that the base 17 forming the ends of the wells 18 is fully supported by the adapter plate 19, so that the grinding means located in the wells 18 cannot pass through the base 17 during the process of breaking down.

Figure 5:
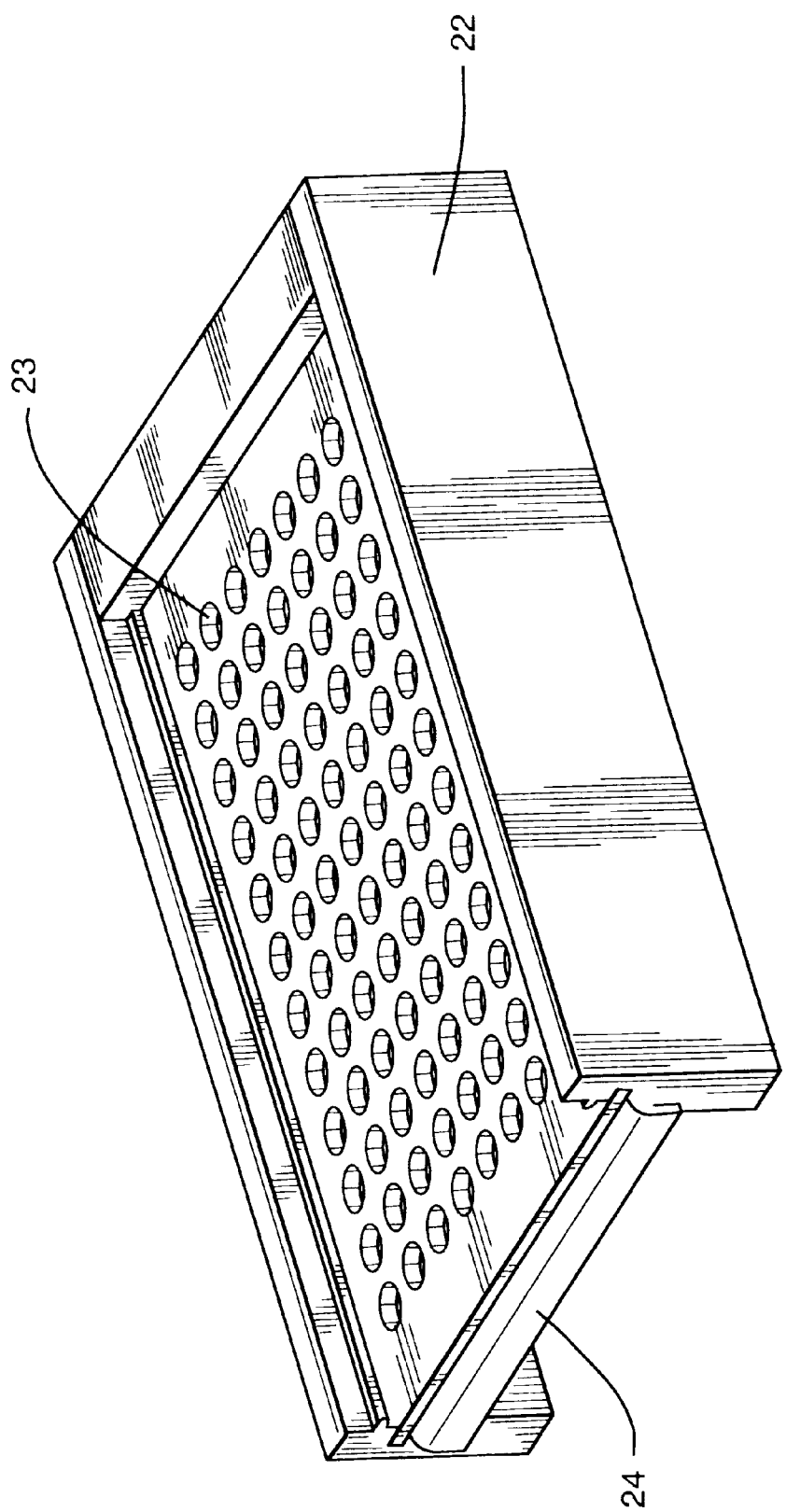
FIG. 5 shows the plate used to insert the grinding means in the wells in the well block, in detailed view.

The plate shown in FIG. 5 can be used to simplify the process of transferring individual grinding means into the wells 18, which is laborious on account of the large number of individual grinding chambers (wells 18) provided according to the invention. For this purpose the plate 22 has openings 23 which are somewhat larger in size than the grinding means formed as balls or beads in the embodiment shown by way of example. A slide 24 is movably mounted on the plate 22 and in the pushed-in position shown in FIG. 5 it forms the base for the openings 23 in the plate 22, so that in this position the grinding means can be inserted in the openings 23. Then the plate 22 is oriented over the well block 16, preferably by means of an interlocking arrangement provided, so that the openings 23 are located so as to register with the wells 18 in the well block 16. When the slide 24 is then pulled out of the plate 22, the grinding means fall into the wells 18.

The process according to the invention is explained in more detail by means of the Examples of applications described below:

1. Parallel break down and lysing of fresh untreated leaf material in a 96 well block in buffer solution About 50 mg of fresh leaf material from wheat plants were placed in each 1.2 ml cavity in a standard commercial 96 well plate (e.g. QIAGEN). A grinding ball made of tungsten carbide (3 mm in diameter) was added to each sample using the apparatus shown in FIG. 5. 400 μl of lysing buffer I (50 mM TRIS/HCl pH 8.0, 10 mM EDTA ph 8.0, 100 mM NaCl, 1% SDS), 2 μl of RNase A (100 mg/ml) and 2 μl of an antifoamer (e.g. antifoam A, SIGMA) were pipetted into each cavity. The 96 well plate was sealed using suitable closure caps and placed in the adapter plates (FIG. 4). The plate sandwich (FIG. 3), consisting of a 96 well plate and upper and lower adapter plates, was clamped in the holder of the vibrating ball mill. The vibrating ball mill was operated at a frequency of 30 l/s for 2 minutes. The plate sandwich was removed from the holder, the 96 well plate was rotated through 180° and then put back in the adapter plates. The plate sandwich was once more clamped in the vibrating mill, but this time, thanks to the rotation of the 96 well plate, the positions which had previously been on the inside and had a smaller radius of oscillation were now on the outside and vice versa. The process was continued for a further 2 minutes at 30 l/s. For the subsequent isolation of the nucleic acids, proteins and polysaccharides were precipitated by the addition of 140 μl of 3M potassium acetate. Cell debris and precipitates were removed by centrifuging and the DNA was isolated from the supernatant. To do this, the DNA was bound to a silica gel membrane and eluted after repeated washing in 200 μl of buffer AE (10 mM TRIS/HCl pH 9.0, 0.5 mM EDTA). The DNA yield was about 1 μg of DNA/10 mg of leaf material. From 2 μl of eluate, a non-coding region of the chloroplast DNA was amplified in a PCR reaction using universal primers (Taberlet et al. 1991).

2. Parallel breaking down and lysing of fresh untreated leaf material in a 96 well block in buffer solution: checking for cross-contamination About 50 mg of fresh leaf material from wheat plants were placed in a standard commercial 96 well plate having 1.2 ml cavities (e.g. QIAGEN). Leaf material was placed in only every second cavity in the 96 well plate. As described in Example 1, grinding balls, lysing buffer, RNase A and antifoamers were added to each cavity. The breaking up, lysing and subsequent DNA isolation and PCR amplification were carried out as described in Example 1.

The amplified material was transferred to an agarose gel and stained with ethidium bromide. Whereas in the positions filled with plant material DNA bands of the expected size were obtained, no DNA bands were visible on the agarose gel in the samples without plant material. The breaking down process does not result in cross-contamination.

3. Breaking down frozen leaf material in a 96 well block using liquid nitrogen

About 50 mg of leaf material from wheat plants were placed in every 1.2 ml cavity of a standard commercial 96 well plate (e.g. QIAGEN). The 96 well plate was closed off using suitable closure caps and the samples were stored for several days by deep freezing at −80° C. until required for further use.

For the breaking down process and subsequent DNA isolation, the 96 well plate was pre-cooled in liquid nitrogen. A grinding ball made of stainless steel (diameter 3 mm) was added to each cavity using the device shown in FIG. 5 (ball dispenser). The wells were sealed, the 96 well plate cooled again in liquid nitrogen and then inserted in the corresponding adapter plates. The plate sandwich consisting of a 96 well plate and upper and lower adapter plates was clamped in the holder of the vibrating ball mill. The mill was operated for 1 minute at a frequency of 20 l/s. The plate sandwich was removed from the holder, the 96 well plate was cooled in nitrogen once more and, after being rotated through 180°, put back into the adapter plates. The plate sandwich was then returned to the vibrating ball mill, in which, as a result of the rotation of the 96 well plate, the positions which had previously been on the inside and had a smaller oscillating radius were now on the outside and vice versa. The breaking down process was continued for 1 minute at 20 l/s. 400 μl of lysing buffer I (preheated to 80° C.) and 2 μl of RNase A (100 mg/l) were added to the powdered material. Salt precipitation, DNA isolation and PCR amplification were carried out as in Example 1.

The yield of DNA was about 1 μg of DNA/10 mg of leaf material. The desired sequence could be successfully amplified from all the samples.

What is claimed is:

1. A process for breaking down multiple biological samples simultaneously in a vibrating ball mill for isolating proteins and/or nucleic acids comprising the steps of:

disposing each of the biological samples in a well of a multi-well block (16) having more than 10 wells, wherein each well containing a biological sample is provided with a grinding means and a lid to close off the well and wherein the well block is clamped in a U-shaped holder of the ball mill, which holder has two opposing retaining arms, wherein one of the retaining arms is movably mounted for clamping the well block into the holder by means of an adjustment and clamping screw, and which holder prevents rotation of the well block by means of cams, which protrude above the planes of the base and the lid on the well block and which interlockingly engage in recesses in each of the retaining arms of the holder, wherein the depth of the recesses corresponds to the height of the cams;

subjecting the biological samples and grinding means in the well block to input energy sufficient to break down the biological samples; and isolating proteins and/or nucleic acids from the broken down samples.

2. The process according to claim 1, wherein the biological sample is pretreated.

3. The process according to claim 1, wherein DNA and/or RNA is isolated from the broken down biological samples.

4. The process according to claim 1, wherein a subsequent manipulation and/or analysis of the proteins and/or nucleic acids is carried out.

5. The process according to claim 1, wherein the breaking down is carried out in the presence of adjuvants.

6. The process according to claim 1, wherein the breaking down is carried out in the presence of lysing agents and/or stabilizers.

7. The process according to claim 1, wherein the biological material or the biological sample is selected from the group consisting of a food sample which contains free or bound nucleic acids or cells containing nucleic acids, an environmental sample which contains free or bound nucleic acids or cells containing nucleic acids, a cell-free sample material, plasma, body fluids, blood, sputum, urine, feces, sperm, cells or cell cultures, serum, leukocyte fractions, smears, tissue samples of all kinds, plants and parts of plants, microorganisms, bacteria, viruses, yeasts, embryos, fungi, and combinations thereof.

8. A vibrating ball mill apparatus adapted for use with multi-well blocks, having containers to be clamped therein in a U-shaped holder having two opposing retaining arms, one of the retaining arms being movably mounted for clamping the container and having an adjustment and clamping screw, and wherein individual grinding means are placed in the containers in order to supply energy for comminution, wherein the containers are constructed as unified well blocks having a plurality of grinding chambers, which are wells incorporated therein and closed off by means of a lid or a plurality of lids placed on the well block and the well blocks are adapted to be secured, by interlocking engagement in the holder having rotation prevention means, by integral cams protruding above the plane thereof, and wherein the retaining arms of the holder each have a recess, corresponding in depth to the height of the cams, for interlockingly receiving the cams.

9. The apparatus according to claim 8, wherein a cam is provided on both the base and lid of the well blocks so as to project above the plane thereof.

10. The apparatus according to claim 8, wherein the base of the well block has a cam projecting above its plane and an adapter plate interlockingly engaging over the lid is provided with a cam projecting above the plane thereof.

11. The apparatus according to claim 8, wherein the cams engaging in the recesses in the retaining arms of the holder are formed on an adapter plate interlockingly engaging over the base or lid of the well block which is to be clamped in place as the grinding container.

12. The apparatus according to claim 11, wherein the adapter plate engaging over the base of the well block has a groove for accommodating an upstand projecting from the base of the well block so that the base lies flush against the adapter plate.

13. The apparatus according to one of claims 8 to 12 wherein as rotation prevention means the cams are arranged so that the well block clamped in the holder rests on the base plate of the U-shaped holder.

14. The apparatus according to one of claims 8 to 12, wherein as rotation prevention means the cams and recess have mutually corresponding shapes in profile.

15. The apparatus according to claims 8 to 12, wherein in order to place the grinding means in the grinding chambers of a well block, a plate which is to be oriented on the well block is provided with openings associated with the individual grinding chambers of the well block and with a slide displaceably mounted on the plate and forming a movable base for the openings in the plate for securing the grinding means placed in the openings.

16. The apparatus according to claim 15, wherein the grinding means are in the form of beads or balls.

17. The apparatus according to claim 13, wherein in order to place the grinding means in the grinding chambers of a well block, a plate which is to be oriented on the well block is provided with openings associated with the individual grinding chambers of the well block and with a slide displaceably mounted on the plate and forming a movable base for the openings in the plate for securing the grinding means placed in the openings.

18. The apparatus according to claim 14, wherein in order to place the grinding means in the grinding chambers of a well block, a plate which is to be oriented on the well block is provided with openings associated with individual grinding chambers of the well block and with a slide displaceably mounted on the plate and forming a movable base for the openings in the plate for securing the grinding means placed in the openings.

* * * * *

UNITED STATES PATENT AND TRADEMARK OFFICE
CERTIFICATE OF CORRECTION

| | | |
|---|---|---|
| PATENT NO. | : 6,258,930 B1 | Page 1 of 1 |
| DATED | : July 10, 2001 | |
| INVENTOR(S) | : Gauch, Bastian, Roord, Orth, and Angeel | |

It is certified that error appears in the above-identified patent and that said Letters Patent is hereby corrected as shown below:

<u>Title page,</u>
Item [73], the correct Assignees are:
    Qiagen GmbH, Hilden (DE)
    F. Kurt Retsch GmbH & Co. KG, Haan (DE)

Signed and Sealed this

Nineteenth Day of February, 2002

Attest:

*Attesting Officer*

JAMES E. ROGAN
*Director of the United States Patent and Trademark Office*